(12) United States Patent
Djupesland et al.

(10) Patent No.: US 12,083,270 B2
(45) Date of Patent: Sep. 10, 2024

(54) DELIVERY DEVICE AND METHOD

(75) Inventors: Per Gisle Djupesland, Oslo (NO);
Roderick Peter Hafner, Swindon (GB); Colin David Sheldrake, Oxfordshire (GB)

(73) Assignee: OptiNose Inc., Yardley, PA (US)

( * ) Notice: Subject to any disclaimer, the term of this patent is extended or adjusted under 35 U.S.C. 154(b) by 1510 days.

(21) Appl. No.: 12/279,285

(22) PCT Filed: Feb. 14, 2007

(86) PCT No.: PCT/GB2007/000516
§ 371 (c)(1),
(2), (4) Date: Nov. 13, 2009

(87) PCT Pub. No.: WO2007/093791
PCT Pub. Date: Aug. 23, 2007

(65) Prior Publication Data
US 2010/0057047 A1 Mar. 4, 2010

(30) Foreign Application Priority Data
Feb. 14, 2006 (GB) ..................... 0602980

(51) Int. Cl.
*A61M 15/08* (2006.01)
*A61M 11/00* (2006.01)
*A61M 15/00* (2006.01)

(52) U.S. Cl.
CPC ........ *A61M 15/0098* (2014.02); *A61M 11/00* (2013.01); *A61M 15/0021* (2014.02);
(Continued)

(58) Field of Classification Search
None
See application file for complete search history.

(56) References Cited

U.S. PATENT DOCUMENTS 605,436 A 6/1898 Kellogg
642,748 A 2/1900 Manners
(Continued)

FOREIGN PATENT DOCUMENTS

| GB | 240565 | * 10/2004 | ............ A61M 15/08 |
| WO | WO 96/22802 | 8/1996 | |

(Continued)

OTHER PUBLICATIONS

U.S. Appl. No. 12/973,317, Djupesland.
(Continued)

*Primary Examiner* — Annette Dixon
(74) *Attorney, Agent, or Firm* — Finnegan, Henderson, Farabow, Garrett & Dunner, LLP

(57) ABSTRACT

A nasal delivery device for and method of delivering substance to the middle meatus in a nasal cavity of a subject in the treatment of a condition, in particular an inflammatory or infectious condition, thereof, the delivery device comprising: a nosepiece unit (17) including a nosepiece (20) for fitting to a nostril of a subject and a nozzle (25) through which substance is in use delivered to the respective nasal cavity; and a delivery unit (29) for delivering substance through the nozzle of the nosepiece; wherein the delivery device is configured to provide for deposition of a significant fraction of the delivered dose on, around and in the vicinity of the middle meatus.

13 Claims, 6 Drawing Sheets

Figure 1:
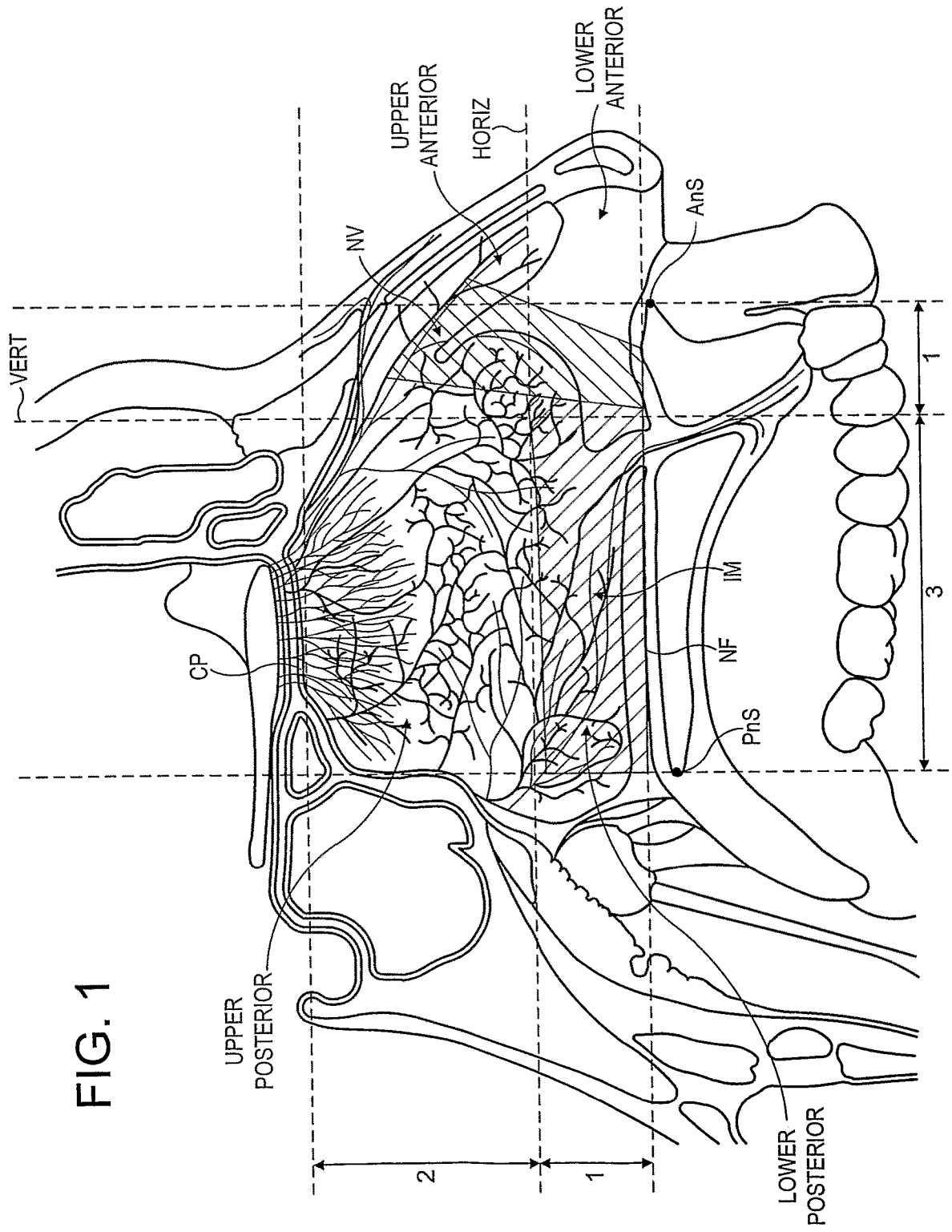

(52) U.S. Cl.
CPC .......... *A61M 15/009* (2013.01); *A61M 15/08* (2013.01); *A61M 15/0091* (2013.01); *A61M 2210/0681* (2013.01)

(56) References Cited

U.S. PATENT DOCUMENTS

| | | | |
|---|---|---|---|
| 746,749 A | 12/1903 | Seidel | |
| 5,645,046 A * | 7/1997 | Kay | 128/201.18 |
| 5,797,392 A | 8/1998 | Keldmann et al. | |
| 6,012,454 A * | 1/2000 | Hodson | A61M 15/0028 |
| | | | 128/203.15 |
| 6,253,762 B1 * | 7/2001 | Britto | A61M 15/009 |
| | | | 128/200.14 |
| 6,470,882 B1 * | 10/2002 | Newhouse et al. | 128/200.24 |
| 6,648,848 B1 | 11/2003 | Keldmann et al. | |
| 6,715,485 B1 * | 4/2004 | Djupesland | 128/203.15 |
| D530,815 S | 10/2006 | Murphy et al. | |
| 7,347,201 B2 | 3/2008 | Djupesland | |
| 7,377,901 B2 | 5/2008 | Djupesland et al. | |
| 7,481,218 B2 | 1/2009 | Djupesland | |
| 7,543,581 B2 | 6/2009 | Djupesland | |
| 7,740,014 B2 | 6/2010 | Djupesland | |
| 7,784,460 B2 | 8/2010 | Djupesland et al. | |
| 7,841,337 B2 | 11/2010 | Djupesland | |
| 7,854,227 B2 | 12/2010 | Djupesland | |
| 7,934,503 B2 | 5/2011 | Djupesland et al. | |
| 7,975,690 B2 | 6/2011 | Djupesland | |
| 8,047,202 B2 | 11/2011 | Djupesland | |
| 8,146,589 B2 | 4/2012 | Djupesland | |
| 8,171,929 B2 | 5/2012 | Djupesland et al. | |
| 8,327,844 B2 | 12/2012 | Djupesland | |
| 8,511,303 B2 | 8/2013 | Djupesland | |
| 8,522,778 B2 | 9/2013 | Djupesland | |
| 8,550,073 B2 | 10/2013 | Djupesland | |
| 8,555,877 B2 | 10/2013 | Djupesland | |
| 8,555,878 B2 | 10/2013 | Djupesland | |
| 8,590,530 B2 | 11/2013 | Djupesland et al. | |
| 8,596,278 B2 | 12/2013 | Djupesland | |
| 8,800,555 B2 | 8/2014 | Djupesland | |
| 8,875,704 B2 | 11/2014 | Djupesland et al. | |
| 8,899,229 B2 | 12/2014 | Djupesland et al. | |
| 8,910,629 B2 | 12/2014 | Djupesland et al. | |
| D723,156 S | 2/2015 | Djupesland et al. | |
| D725,769 S | 3/2015 | Djupesland et al. | |
| 8,978,647 B2 | 3/2015 | Djupesland et al. | |
| 9,010,325 B2 | 4/2015 | Djupesland et al. | |
| 9,038,630 B2 | 5/2015 | Djupesland et al. | |
| 9,067,034 B2 | 6/2015 | Djupesland et al. | |
| 9,072,857 B2 | 7/2015 | Djupesland | |
| 9,108,015 B2 | 8/2015 | Djupesland | |
| 9,119,932 B2 | 9/2015 | Djupesland | |
| 9,132,249 B2 | 9/2015 | Djupesland | |
| 9,144,652 B2 | 9/2015 | Djupesland et al. | |
| 9,168,341 B2 | 10/2015 | Djupesland | |
| 9,205,208 B2 | 12/2015 | Djupesland | |
| 9,205,209 B2 | 12/2015 | Djupesland | |
| 9,272,104 B2 | 3/2016 | Djupesland | |
| D759,805 S | 6/2016 | Djupesland | |
| D761,951 S | 7/2016 | Djupesland | |
| 2003/0079742 A1 | 5/2003 | Giroux | |
| 2003/0217748 A1 | 11/2003 | Giroux | |
| 2004/0024330 A1 | 2/2004 | Djupesland et al. | |
| 2004/0037809 A1 | 2/2004 | Quay et al. | |
| 2004/0112378 A1 * | 6/2004 | Djupesland | A61B 5/085 |
| | | | 128/203.12 |
| 2004/0112379 A1 | 6/2004 | Djupesland | |
| 2004/0112380 A1 | 6/2004 | Djupesland | |
| 2004/0149289 A1 * | 8/2004 | Djupesland | 128/207.18 |
| 2004/0182388 A1 | 9/2004 | Djupesland | |
| 2005/0028812 A1 | 2/2005 | Djupesland | |
| 2005/0043706 A1 | 2/2005 | Eaton et al. | |
| 2005/0072430 A1 | 4/2005 | Djupesland | |
| 2005/0235992 A1 | 10/2005 | Djupesland | |
| 2005/0240147 A1 | 10/2005 | Makower et al. | |
| 2006/0002861 A1 | 1/2006 | Biggadike | |
| 2006/0096589 A1 | 5/2006 | Djupesland | |
| 2006/0107957 A1 | 5/2006 | Djupesland | |
| 2006/0169278 A1 | 8/2006 | Djupesland et al. | |
| 2006/0219240 A1 | 10/2006 | Djupesland | |
| 2006/0219241 A1 | 10/2006 | Djupesland | |
| 2006/0225732 A1 | 10/2006 | Djupesland | |
| 2006/0231094 A1 | 10/2006 | Djupesland | |
| 2006/0260606 A1 | 11/2006 | Coifman | |
| 2006/0276552 A1 * | 12/2006 | Barbut | A61F 7/12 |
| | | | 514/743 |
| 2007/0039614 A1 | 2/2007 | Djupesland | |
| 2007/0125371 A1 | 6/2007 | Djupesland | |
| 2007/0129665 A1 * | 6/2007 | Dickens | A61M 15/0028 |
| | | | 604/26 |
| 2007/0186927 A1 | 8/2007 | Djupesland et al. | |
| 2008/0156319 A1 | 7/2008 | Avni | |
| 2008/0161771 A1 | 7/2008 | Djupesland | |
| 2008/0163874 A1 | 7/2008 | Djupesland | |
| 2008/0200848 A1 | 8/2008 | Avni | |
| 2008/0221471 A1 | 9/2008 | Djupesland et al. | |
| 2008/0223363 A1 | 9/2008 | Djupesland | |
| 2008/0289629 A1 | 11/2008 | Djupesland et al. | |
| 2009/0025713 A1 | 1/2009 | Keller et al. | |
| 2009/0101146 A1 | 4/2009 | Djupesland | |
| 2009/0293873 A1 | 12/2009 | Djupesland et al. | |
| 2009/0304802 A1 | 12/2009 | Djupesland et al. | |
| 2009/0314293 A1 | 12/2009 | Djupesland | |
| 2009/0320832 A1 | 12/2009 | Djupesland | |
| 2010/0035805 A1 | 2/2010 | Hafner | |
| 2010/0051022 A1 | 3/2010 | Djupesland et al. | |
| 2010/0057047 A1 | 3/2010 | Djupesland et al. | |
| 2010/0242959 A1 | 9/2010 | Djupesland et al. | |
| 2010/0282246 A1 | 11/2010 | Djupesland et al. | |
| 2010/0288275 A1 | 11/2010 | Djupesland et al. | |
| 2010/0300439 A1 | 12/2010 | Djupesland et al. | |
| 2011/0023869 A1 | 2/2011 | Djupesland | |
| 2011/0053827 A1 | 3/2011 | Hafner | |
| 2011/0088690 A1 | 4/2011 | Djupesland et al. | |
| 2011/0088691 A1 | 4/2011 | Djupesland | |
| 2011/0114087 A1 | 5/2011 | Djupesland et al. | |
| 2011/0126830 A1 | 6/2011 | Djupesland et al. | |
| 2011/0259329 A1 | 10/2011 | Djupesland et al. | |
| 2011/0318345 A1 | 12/2011 | Djupesland | |
| 2012/0000459 A1 | 1/2012 | Djupesland | |
| 2012/0006323 A1 | 1/2012 | Djupesland | |
| 2012/0073571 A1 | 3/2012 | Djupesland | |
| 2012/0090608 A1 | 4/2012 | Djupesland et al. | |
| 2012/0260915 A1 | 10/2012 | Djupesland | |
| 2013/0098362 A1 | 4/2013 | Djupesland et al. | |
| 2013/0125889 A1 | 5/2013 | Djupesland et al. | |
| 2013/0327320 A1 | 12/2013 | Djupesland | |
| 2014/0018295 A1 | 1/2014 | Djupesland | |
| 2014/0041660 A1 | 2/2014 | Djupesland et al. | |
| 2014/0060536 A1 | 3/2014 | Djupesland | |
| 2014/0073562 A1 | 3/2014 | Djupesland | |
| 2014/0144442 A1 | 5/2014 | Djupesland et al. | |
| 2014/0144443 A1 | 5/2014 | Djupesland et al. | |
| 2014/0166008 A1 | 6/2014 | Djupesland | |
| 2014/0202456 A1 | 7/2014 | Djupesland | |
| 2014/0246022 A1 | 9/2014 | Djupesland et al. | |
| 2015/0007811 A1 | 1/2015 | Djupesland et al. | |
| 2015/0013670 A1 | 1/2015 | Djupesland et al. | |
| 2015/0013677 A1 | 1/2015 | Djupesland et al. | |
| 2015/0053201 A1 | 2/2015 | Djupesland et al. | |
| 2015/0090259 A1 | 4/2015 | Djupesland et al. | |
| 2015/0101605 A1 | 4/2015 | Djupesland et al. | |
| 2015/0144129 A1 | 5/2015 | Djupesland et al. | |
| 2015/0165139 A1 | 6/2015 | Hafner | |
| 2015/0182709 A1 | 7/2015 | Djupesland | |
| 2015/0246194 A1 | 9/2015 | Djupesland et al. | |
| 2015/0367090 A1 | 12/2015 | Djupesland et al. | |
| 2015/0367091 A1 | 12/2015 | Djupesland et al. | |
| 2016/0001022 A1 | 1/2016 | Djupesland et al. | |
| 2016/0045687 A1 | 2/2016 | Djupesland | |
| 2016/0051778 A1 | 2/2016 | Djupesland et al. | |
| 2016/0074603 A1 | 3/2016 | Djupesland et al. | |
| 2016/0082206 A1 | 3/2016 | Djupesland et al. | |
| 2016/0082207 A1 | 3/2016 | Djupesland et al. | |

(56) References Cited

U.S. PATENT DOCUMENTS

| | | |
|---|---|---|
| 2016/0166788 A1 | 6/2016 | Djupesland et al. |
| 2016/0184537 A1 | 6/2016 | Djupesland |
| 2016/0193435 A1 | 7/2016 | Djupesland |

FOREIGN PATENT DOCUMENTS

| | | |
|---|---|---|
| WO | WO 98/53869 | 12/1998 |
| WO | 1999/049923 | 10/1999 |
| WO | 2000/041816 | 7/2000 |
| WO | 2000/051672 | 9/2000 |
| WO | WO 00/51672 | 9/2000 |
| WO | WO 01/97689 | 12/2001 |
| WO | WO 02/068029 | 9/2002 |
| WO | WO 02/068030 | 9/2002 |
| WO | WO 02/068031 | 9/2002 |
| WO | WO 02/068032 | 9/2002 |
| WO | 2003/000310 | 1/2003 |
| WO | WO 03/000310 | 1/2003 |
| WO | WO 03/020350 | 3/2003 |
| WO | WO 03/082393 | 10/2003 |
| WO | WO 03/084591 | 10/2003 |
| WO | WO 03/090812 | 11/2003 |
| WO | WO 2004/004814 | 1/2004 |
| WO | WO 2004/004922 | 1/2004 |
| WO | WO2004060433 * | 7/2004 |
| WO | WO 2004/103447 | 12/2004 |
| WO | WO 2005/016423 | 2/2005 |
| WO | WO 2005/021059 | 3/2005 |
| WO | WO 2006/030210 | 3/2006 |
| WO | WO 2006/090149 | 8/2006 |
| WO | 2006/124954 | 11/2006 |
| WO | WO 2007/083073 | 7/2007 |
| WO | WO 2007/093784 | 8/2007 |
| WO | WO 2007/093791 | 8/2007 |
| WO | WO 2007/099361 | 9/2007 |
| WO | WO 2007/102089 | 9/2007 |
| WO | WO 2007/107887 | 9/2007 |
| WO | WO 2007/125318 | 11/2007 |
| WO | WO 2007/141541 | 12/2007 |
| WO | WO 2008/012531 | 1/2008 |
| WO | WO 2008/065403 | 6/2008 |
| WO | WO 2008/081326 | 7/2008 |
| WO | WO 2008/081327 | 7/2008 |
| WO | WO 2008/122791 | 10/2008 |
| WO | WO 2008/122795 | 10/2008 |
| WO | WO 2009/044172 | 4/2009 |
| WO | WO 2010/029441 | 3/2010 |
| WO | WO 2012/035427 | 3/2012 |
| WO | WO 2012/123819 | 9/2012 |
| WO | WO 2013/124491 | 8/2013 |
| WO | WO 2013/124492 | 8/2013 |
| WO | WO 2013/124493 | 8/2013 |
| WO | WO 2014/155192 | 10/2014 |

OTHER PUBLICATIONS

U.S. Appl. No. 13/063,963, Djupesland et al.
U.S. Appl. No. 13/099,183, Djupesland et al.
U.S. Appl. No. 13/180,492, Djupesland.
U.S. Appl. No. 13/244,499, Djupesland.
International Search Report for International App. No. PCT/GB2007/000516 Date of Mailing Aug. 27, 2007 (6 pages).
Written Opinion of the International Search Report for International App. No. PCT/GB2007/000516 Date of Mailing Aug. 27, 2007 (11 pages).
International Preliminary Report on Patentability App. No. PCT/GB2007/000516 Date of Mailing Aug. 27, 2007 (11 pages).
Cindy H. Dubin, *Nothing to Sneeze at*, Pharmaceutical Formulation & Quality Magazine (Jan. 29, 2003).
Per Gisle Djupesland, *Nasal Delivery of Vaccines*, EPC (Jan. 29, 2003).
Per Gisle Djupesland, *Who Nose How Far Nasal Delivery Can Go?*, EPC (Oct. 7, 2003).
Per Gisle Djupesland, *Bi-directional Nasal Drug Delivery*, Innovations in Pharmaceutical Technology (Jul. 10, 2004).
P.G. Djupesland, *Bi-Directional Nasal Delivery of Aerosols Can Prevent Lung Deposition*, Journal of Aerosol Medicine (Sep. 2004).
*Bi-Directional Nasal Device Delivers Drug on Exhalation*, Pharmaceutical Technology (Sep. 10, 2004).
Ola Dale et al., *Intranasal Midazolam: A Comparison of Two Delivery Devices in Human Volunteers*, Journal of Pharmacy and Pharmacology (Oct. 2004).
M. Kleven, *Using Computational Fluid Dynamics (CFD) to Improve the Bi-Directional Nasal Drug Delivery Concept*, Trans IChemE Part C. (Jun. 2005).
Per Gisle Djupesland, *Breath-Actuated Bi-Directional Delivery Sets the Nasal Market on a New Course*, ONdrugDelivery (Oct. 10, 2005).
Hilde Bakke et al., *Oral Spray Immunization May be an Alternative to Intranasal Vaccine Delivery to Induce Systemic Antibodies but Not Nasal Mucosal or Cellular Immunity*, Scan J. of Immunol. (Mar. 2006).
P.G. Djupesland et al., *Breath Actuated Nasal Device Improves Delivery to Target Sites Beyond the Nasal Valve*, The Laryngoscope (Mar. 2006).
R. Luthringer et al., *Rapid Absorption of Sumatriptan Powder and Effects on Glyceryl tinitrate Model of Headache Following Intranasal Delivery Using a Novel Bi-Directional Device*, Journal of Pharmacy and Pharmacology (Jan. 2009).
A. Skretting et al., *A New Method for Scintigraphic Quantification of Deposition and Clearance in Anatomical Regions of the Human Nose*, Nuclear Medicine Communications (Aug. 2009).
Vickovia et al., *Effective Treatment of Mild-to-Moderate Nasal Polyposis with Fluticasone Delivered by a Novel Device*, Rhinology (Oct. 22, 2009).
Per Gisle Djupesland et al., *Impact of Baseline Nasal Polyp Size and Previous Surgery on Efficacy of Fluticasone Delivered With a Novel Device: A Subgroup Analysis*, Am. J. Rhinology Allergy (2010).
P.G. Djupesland et al., *Intranasal Sumatriptan Powder Delivered by a Novel Breath Actuated Bi-Directional Device for the Acute Treatment of Migraine: A Randomised Placebo-Controlled Study*, Cephalalgia (Mar. 17, 2010).
F.S. Hansen et al., *Preliminary Efficacy of Fluticasone Delivered by a Novel Device in Recalcitrant Chronic Rhinosinusitis*, Rhinology (Jun. 26, 2010).
Per Gisle Djupesland, *Nasal Drug Delivery Devices: Characteristics and Performance in Clinical Perspective—A Review*, Drug. Deliv. and Transl. Res. (Oct. 18, 2012).
Per Gisle Djupesland, *Nasal Deposition and Clearance in Man: Comparison of a Bidirectional Powder Device and a Traditional Liquid Spray Pump*, Journal of Aerosol Medicine and Pulmonary Drug Delivery (Nov. 2012).
Stewart J. Tepper, *Clinical Implications for Breath-Powered Powder Sumatriptan Intranasal Treatment*, Headache, The American Headache Society (Apr. 29, 2013).
Mohammad Obaidi et al., *Improved Pharmacokinetics of Sumatriptan With Breath Powered Nasal Delivery of Sumatriptan Powder*, Headache, The American Headache Society (May 24, 2013).
Per Gisle Djupesland, *Breath Powdered Nasal Delivery: A New Route to Rapid Headache Relief*, Headache, The American Headache Society (Jun. 4, 2013).
Per Gisle Djupesland et al., *The Nasal Approach to Delivering Treatment for Brain Diseases: An Anatomic, Physiologic, and Delivery Technology Overview*, Therapeutic Delivery (2014).
R.K. Cady et al., *A Randomized Double-Blind, Placebo Controlled Study of Breath Powered Nasal Delivery of Sumatriptan Powder (AVP-825) in the Treatment of Acute Migraine (The TARGET Study)*, Headache (Sep. 8, 2014).
S.J. Tepper et al., *AVP-825 Breath-Powdered Intranasal Delivery System Containing 22 mg Sumatriptan Powder vs. 100 mg Oral Sumatripta in the Acute Treatment of Migraines (The COMPASS Study): A Comparative Randomized Clinical Trial Across Multiple Attacks*, Headache: The Journal of Head and Face Pain (Mar. 29, 2015).
D. S. Quintana et al., *Low-dose Oxytocin Delivered Intranasally with Breath Powdered Device Affects Social-Cognitive Behavior: A*

(56) References Cited

OTHER PUBLICATIONS

*Randomized Four-Way Crossover Trial with Nasal Cavity Dimension Assessment*, Transl Psychiatry (Jul. 14, 2015).
R. Mahmoud, *Breathe Out*, Innovations in Phar, Tech. (Dec. 10, 2015).
Definition of Manual by Merriam-Webster, 12 pages, accessed Mar. 19, 2021.

* cited by examiner

DELIVERY DEVICE AND METHOD

The present invention relates to a delivery device for and a method of treating conditions of the nasal airway, in particular inflammatory or infectious conditions relating to the middle meatus, such as rhinosinusitis (RS), including acute rhinosinusitis (ARS) and chronic rhinosinusitis (CRS), polyposis, sinus pains, auto-immune diseases, including viral, bacterial, allergic and non-allergic diseases, and the common cold.

RS is a prevalent disease, with CRS being the most common chronic disease in the US, with 10 to 15% of the population being affected (US, Vital Health Statistics). In Europe, about 10% of the population suffer from CRS and about 2 to 3% suffer from polyposis, with thus 20 to 30% of subjects with CRS also having polyposis.

The pathology of RS and polyposis generally stems from the middle meatus, where the sinus ostia open to the nasal cavity. In subjects with CRS, the mucosal lining becomes swollen, and, if polyps develop, the polyps obstruct the middle meatus and often the olfactory cleft which opens to the olfactory region. As the polyps develop, the polyps normally extend downwards and backwards, though sometimes forwards. The obstruction becomes more pronounced with polyp size and is always more prominent in the upper parts of the nose.

Currently, treatment is by drops as delivered by pipette or aerosol sprays as delivered by a conventional spray pump. Studies have shown that conventional sprays are inadequate in reaching the middle meatus. Drops can reach the middle meatus, but this requires rigorous patient compliance, insofar as the patients have to adopt particular body positions during delivery, such as the "Mecca" position, which are rarely respected.

It is an aim of the present invention to provide a delivery device for and method of delivering substance to the middle meatus, particularly in the treatment of inflammatory or infectious conditions relating to the middle meatus, in particular ARS, CRS and polyposis.

The present inventors have recognized that an increased delivery of substance to the posterior region of the nasal airway, and in particular the upper posterior region of the nasal airway, as illustrated in FIG. 1, relative to the anterior region of the nasal airway, surprisingly provides for improved delivery to the middle meatus, and in particular in subjects with nasal polyps.

The posterior region of the nasal airway is that region which is posterior of the nasal valve NV, as illustrated in FIG. 1. The nasal valve comprises the anterior bony cavum which contains inferior turbinate erectile tissue and septal erectile tissue, which are supported respectively by compliant ala tissue and the rigid cartilaginous septum (Cole). These elements combine to form a dynamic valve, which extends over several millimetres, that adjusts nasal airflow, and is stabilized by cartilage and bone, modulated by voluntary muscle and regulated by erectile tissue. The lumen of the nasal valve is the section of narrowest cross-sectional area between the posterior and anterior regions of the nasal airway, and is much longer and narrower dorsally than ventrally, and this lumen defines a triangular entrance which extends to the piriform region of the bony cavum. The nasal valve is lined in its anterior part with transitional epithelium, with a gradual transition posterior to respiratory epithelium. The nasal valve and anterior vestibule define roughly the anterior one-third of the nose.

The posterior region of the nasal airway is that region which is lined with respiratory epithelium, which is ciliated, and olfactory epithelium, which comprises nerves which extend downwards through the cribiform plate CP from the olfactory bulb, whereas the anterior region of the nasal airway is that region which is lined with squamous epithelium, which is not ciliated, and transitional epithelium. The olfactory epithelium extends on both the lateral and medial sides of the nasal airway, and typically extends downwards about 1.5 to 2.5 cm.

The upper posterior region is the region above the inferior meatus IM, as illustrated in FIG. 1, and encompasses the middle turbinate, the middle meatus, the sinus ostia in infundibulum (ostia to maxillary, frontal and ethmoidal sinuses), the olfactory region, and the upper branches of the trigeminal nerve, and is that region which includes veins which drain to the venous sinuses that surround the brain.

As illustrated in FIG. 1, the posterior region of the nasal airway is the nasal region posterior of an imaginary vertical plane VERT which is located at a position corresponding to the lower angle of the anterior nasal aperture (aperture piriformis), which corresponds substantially to one-quarter of the distance between the anterior nasal spine AnS, which is a pointed projection at the anterior extremity of the intermaxillary suture, and the posterior nasal spine PnS, which is the sharp posterior extremity of the nasal crest of the hard palate and represents the transition between the nose and the nasopharynx, which corresponds to a distance posterior of the anterior nasal spine AnS of between about 13 mm and about 14 mm (Rosenberger defines the distance between the anterior nasal spine AnS and the posterior nasal spine PnS as being 56 mm in eighteen year old boys and 53.3 mm in eighteen year old girls).

As further illustrated in FIG. 1, the upper region of the nasal airway is an upper segment of the nasal airway which is bounded by the cribiform plate CP and a horizontal plane HORIZ which is located at a position corresponding to one-third of the distance between the nasal floor NF of the nasal airway and the cribiform plate CP, which corresponds to a height of typically between about 13 and about 19 mm above the nasal floor NF (Zacharek et al define the distance from the nasal floor NF to the cribiform plate CP as 46+/−4 mm).

The upper posterior region is thus that upper posterior region which is bounded by the above-defined vertical and horizontal planes VERT, HORIZ.

In one aspect the present invention provides a nasal delivery device for delivering substance, typically as a formulation, to the middle meatus in a nasal cavity of a subject in the treatment of a condition, in particular an inflammatory or infectious condition, thereof, the delivery device comprising: a nosepiece unit including a nosepiece for fitting to a nostril of a subject and a nozzle through which substance is in use delivered to the respective nasal cavity; and a delivery unit for delivering substance through the nozzle of the nosepiece; wherein the delivery device is configured such that at least 50% of the dose as initially deposited in the nasal airway is deposited in a region of the nasal cavity which is posterior of the nasal valve and at least 30% of the dose as initially deposited in the nasal cavity is deposited in an upper posterior region of the nasal cavity which is posterior of the nasal valve and above the inferior meatus.

In another aspect the present invention provides a nasal delivery device for delivering substance, typically as a formulation, to the middle meatus in a nasal cavity of a subject in the treatment of a condition, in particular an inflammatory or infectious condition, thereof, the delivery device comprising: a nosepiece unit including a nosepiece for fitting to a nostril of a subject and a nozzle through which substance is in use delivered to the respective nasal cavity; and a delivery unit for delivering substance through the nozzle of the nosepiece; wherein the nozzle provides for delivery of the substance as at least one liquid jet or an aerosol spray having a cone angle of not more than about 50 degrees.

In a further aspect the present invention provides a nasal delivery device for delivering substance, typically as a formulation, to a nasal airway of a subject, comprising: a nosepiece unit including a nosepiece for fitting to a nostril of a subject, the nosepiece including a nozzle through which substance is in use delivered to the respective nasal cavity; and a delivery unit for delivering substance through the nozzle of the nosepiece.

In a still further aspect the present invention provides a method of delivering substance, typically as a formulation, to the middle meatus in a nasal cavity of a subject in the treatment of a condition, in particular an inflammatory or infectious condition, thereof, the method comprising the steps of: fitting a nosepiece unit to one nostril of a subject, the nosepiece unit including a nosepiece which is inserted into the one nostril of a subject and a nozzle through which substance is delivered to the respective nasal cavity; and delivering substance through the nozzle into the nasal cavity, wherein at least 50% of the dose as initially deposited in the nasal airway is deposited in a region of the nasal cavity which is posterior of the nasal valve and at least 30% of the dose as initially deposited in the nasal cavity is deposited in an upper posterior region of the nasal cavity which is posterior of the nasal valve and above the inferior meatus.

In still another aspect the present invention provides a method of delivering substance, typically as a formulation, to the middle meatus in a nasal cavity of a subject in the treatment of a condition, in particular an inflammatory or infectious condition, thereof, the method comprising the steps of: fitting a nosepiece unit to one nostril of a subject, the nosepiece unit including a nosepiece which is into the one nostril of a subject and a nozzle through which substance is delivered to the respective nasal cavity; and delivering substance through the nozzle into the nasal cavity, wherein the nozzle provides for delivery of the substance as at least one liquid jet or an aerosol spray having a cone angle of not more than about 50 degrees.

In yet another aspect the present invention provides a method of delivering substance, typically as a formulation, to a nasal airway of a subject, comprising the steps of: fitting a nosepiece unit to one nostril of a subject, the nosepiece unit including a nosepiece which is inserted into the one nostril of a subject and a nozzle through which substance is delivered to the respective nasal cavity; and delivering substance through the nozzle of the nosepiece unit into the nasal cavity.

In still yet another aspect the present invention provides a nasal delivery device for and method of delivering substance, typically as a formulation, to the middle meatus in a nasal cavity of a subject in the treatment of a condition, in particular an inflammatory or infectious condition, thereof, the delivery device comprising: a nosepiece unit including a nosepiece for fitting to a nostril of a subject and a nozzle through which substance is in use delivered to the respective nasal cavity; and a delivery unit for delivering substance through the nozzle of the nosepiece; wherein the delivery device is configured to provide for deposition of a significant fraction of the delivered dose on, around and in the vicinity of the middle meatus.

In one embodiment the present invention provides for the treatment of rhinosinusitis (RS), including acute rhinosinusitis (ARS) and chronic rhinosinusitis (CRS).

In one embodiment the present invention provides for the treatment of nasal polyps.

CRS and polyposis are observed in subjects with Cystic Fibrosis, both paediatric and adult subjects, where the condition is associated with an abnormality in the nasal mucosa, and the present invention has particular application in relation to such treatment.

In one embodiment the present invention provides for the treatment of sinus pains.

In one embodiment the present invention provides for the treatment of auto-immune diseases, including viral, bacterial, allergic and non-allergic diseases, such as antigen-induced diseases.

In one embodiment the present invention provides for the treatment of the common cold.

In one embodiment the substance comprises a steroid, such as fluticasone, budesonide, mometasone, betamethasone, beclomethasone, triamcinolone and flunisoloide, and the pharmaceutically-acceptable salts and derivatives thereof.

In one embodiment the substance comprises a decongestant, such as ephedrine, pseudoephedrine, oxymetazoline, xylometazoline, phenylephrine and phenylpropanolamine, and the pharmaceutically-acceptable salts and derivatives thereof.

In one embodiment the substance comprises a non-steroidal anti-inflammatory, such as sodium cromoglycate, nedocromil sodium, ibuprofen, salicylates, indomethacin, dexketoprofen, ketoprofen, fenbufen, naproxen and diclofenac, and the pharmaceutically-acceptable salts and derivatives thereof.

In one embodiment the substance comprises an anticholinergic, such as ipratropium, tiotropium and oxitropium, and the pharmaceutically-acceptable salts and derivatives thereof.

In one embodiment the substance comprises an antihistamine, such as azelastine, loratidine, brompheniramine, chlorpheniramine, mizolastine, promethazine, doxylamine, desloratidine, triprolidine, clemastine, fexofenadine, cetirizine and levocetirizine, and the pharmaceutically-acceptable salts and derivatives thereof.

In one embodiment the substance comprises a mast cell stabilizer, such as ketotifen, and the pharmaceutically-acceptable salts and derivatives thereof.

In one embodiment the substance comprises a leukotriene antagonist, such as zafirlukast and montelukast, and the pharmaceutically-acceptable salts and derivatives thereof.

In one embodiment the substance comprises a diuretic, such as frusemide, and the pharmaceutically-acceptable salts and derivatives thereof.

In one embodiment the substance comprises an antibiotic, such as amikacin, azithromycin, aztreonan, cefazolin, cefepine, cefonicid, cefaperazone, cefotaxime, cefotetan, cefoxitin, ceftazidime, ceftizoxime, ceftriaxone, cerfuroxime, cephapirin, ciprofloxacin, clindamycin, doxycycline, erthyromycin lactobionate, gentamicin, kanamycin, linezolid, mezlocillin, mupirocin, nafcillin, netilmicin, neomycin, oxacillin, paromomycin, piperacillin, streptomycin, ticarcillin, tobramycin and vancomycin, and the pharmaceutically-acceptable salts and derivatives thereof.

In one embodiment the substance comprises an antifungal, such as polyene macrolides, tetraene macrolides, pentaenic macrolides, fluorinated pryimidines, imidazoles, triazoles, azoles, halogenated phenolic ethers, thiocarbamates, allylamines, sterol inhibitor, amphotericin B, ketoconazole, itraconazole, saperconazole, voriconazole, flucytosine, miconazole, fluconazole, griseofulvin, clotrimazole, econazole, terconazole, butoconazole, oxiconazole, sulconazole, ciclopirox olamine, haloprogin, tolnaftate, naftifine, terbinafine hydrochloride, morpholines, nystatin, natamycin, butenafine, undecylenic acid, Whitefield's ointment, propionic acid, caprylic acid, and the pharmaceutically-acceptable salts and derivatives thereof.

In one embodiment the substance comprises an immuno-modulator. In one embodiment the immuno-modulator comprises an antigen, such as an allergen, in particular a polypeptide antigen or any part, small or large, of an antigen, where natural or synthesized. In another embodiment the immuno-modulator comprises a nucleic acid molecule or polypeptide for modulation or suppression of the immune response or one or more steps in the immune cascade or process.

In one embodiment the substance comprises an ionic transport control substance which acts to normalize or counteract an imbalance in the ionic transport across the cell membranes, such as benzalkonium chloride.

In one embodiment the substance can comprise a biofilm-destroying agent which acts to destroy bacterial bioflims which can tend to form in subjects with conditions associated with nasal inflammation and infection. In one embodiment the biofilm-destroying agent comprises an anti-biotic, such as tetracycline, linezolid and moxifloxacin, and the pharmaceutically-acceptable salts and derivatives thereof. In another embodiment the biofilm-destroying agent comprises a disinfectant, such as chlorohexidine, and the pharmaceutically-acceptable salts and derivatives thereof. In a further embodiment the biofilm-destroying agent can be included as a preservative, such as benzalkonium chloride, within the substance formulation.

In preferred embodiments the substances can be administered separately or in any combination, individually or simultaneously, within a single formulation.

Figure 2:
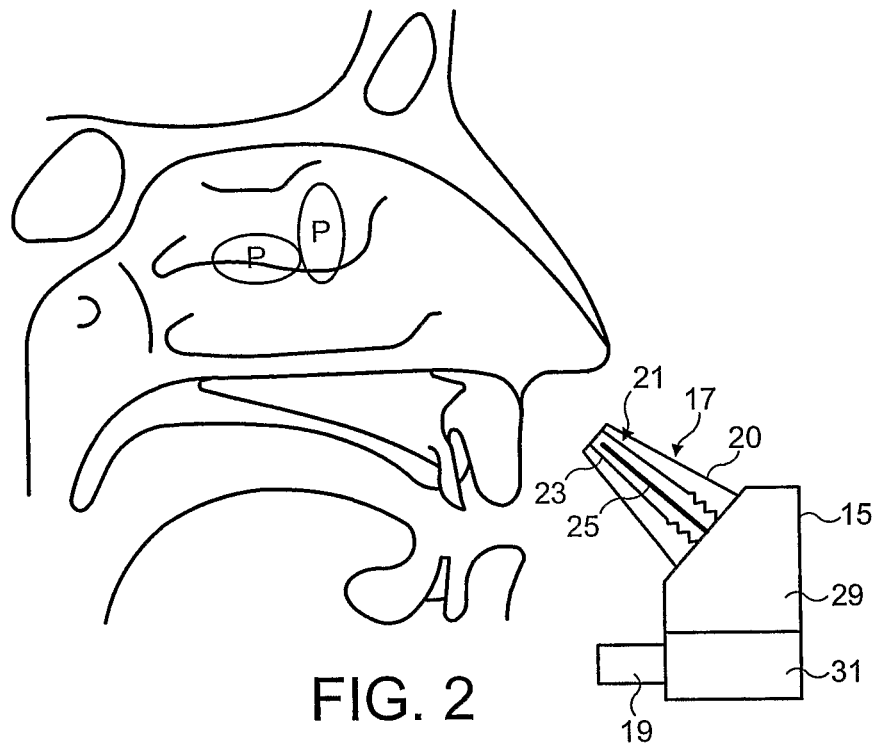
Figure 3:
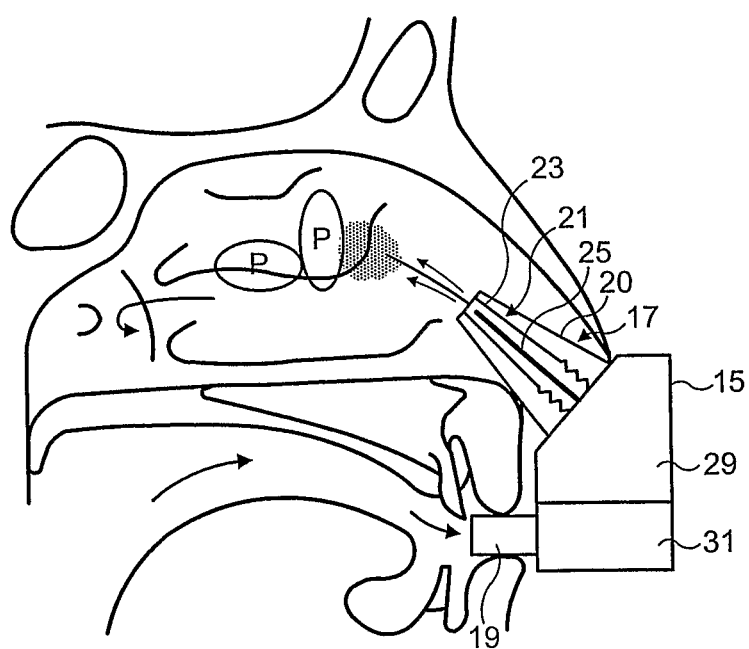
Figure 4:
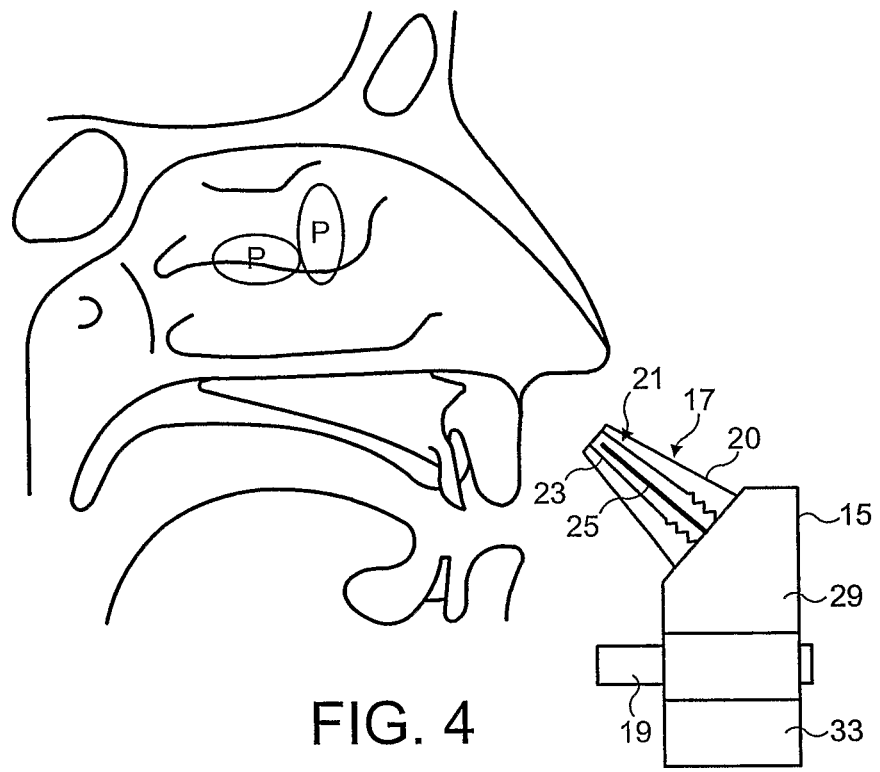
Figure 5:
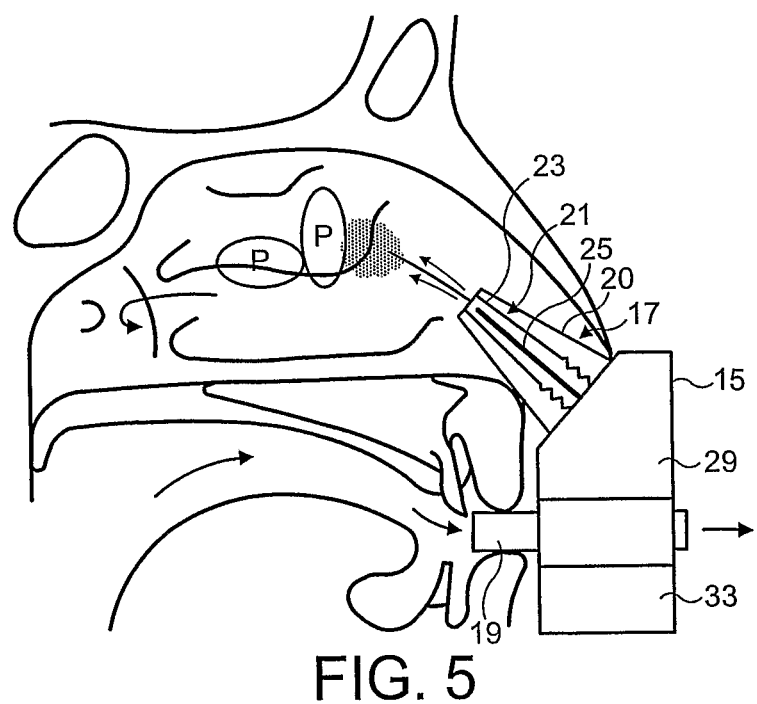
Figure 6:
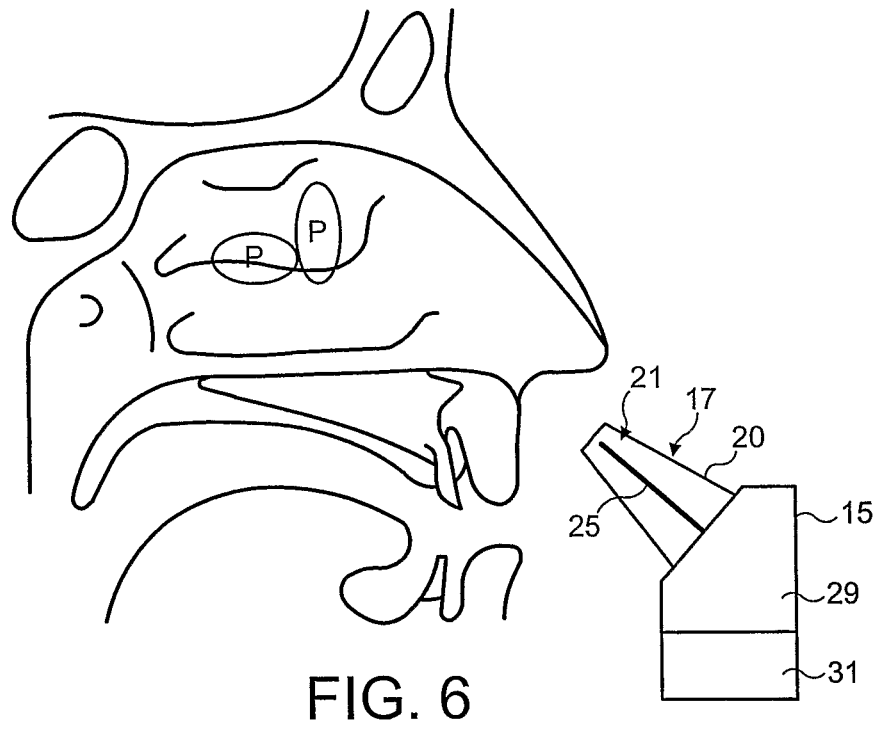
Figure 7:
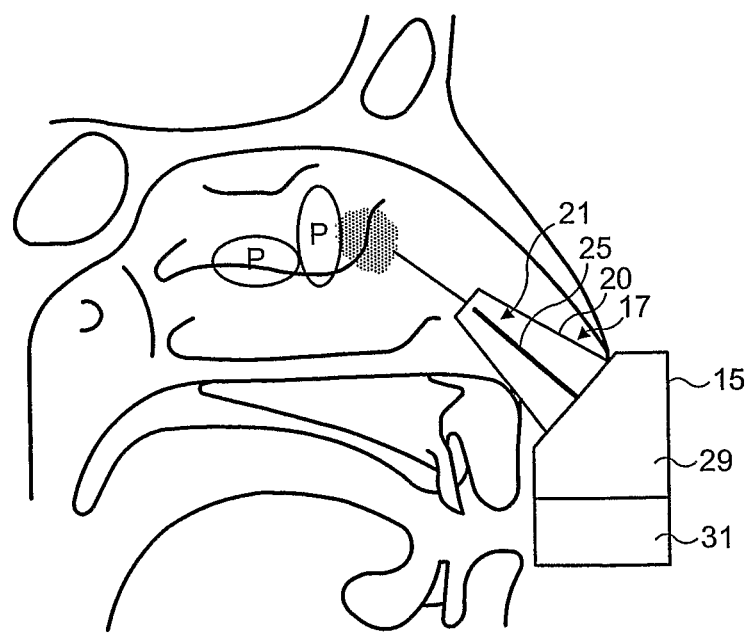
Figure 8:
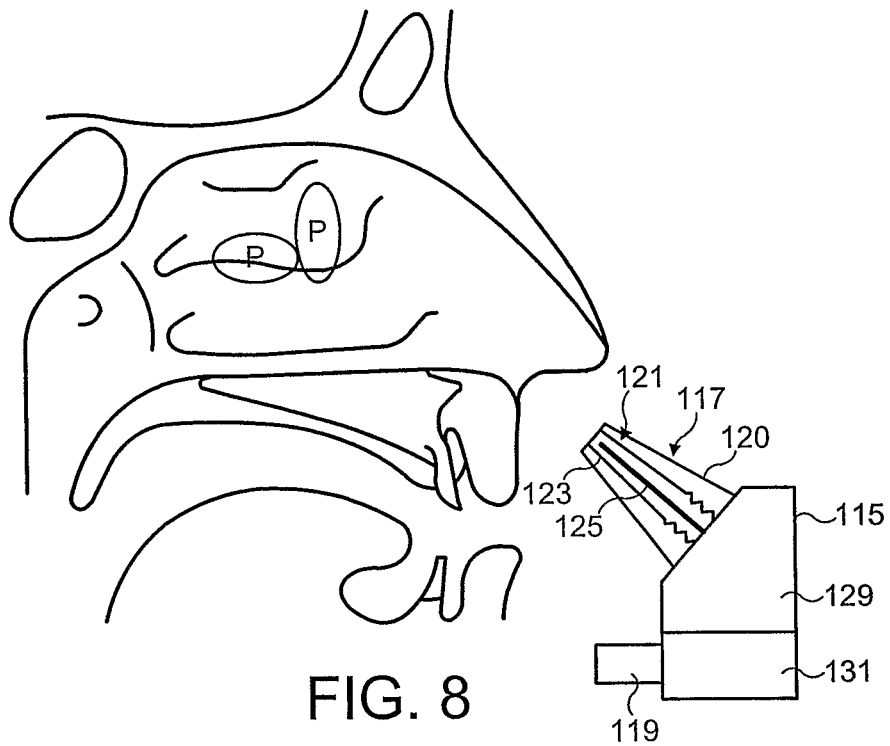
Figure 9:
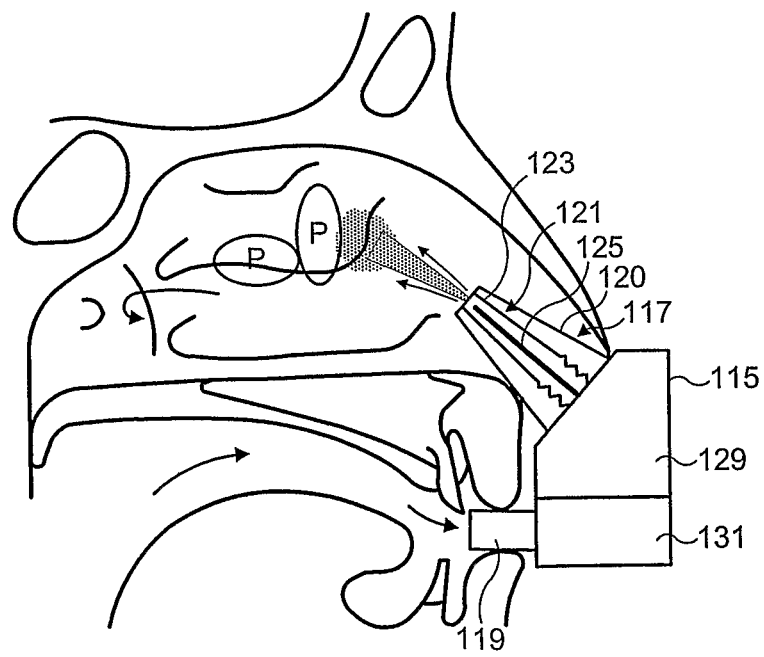
Figure 10:
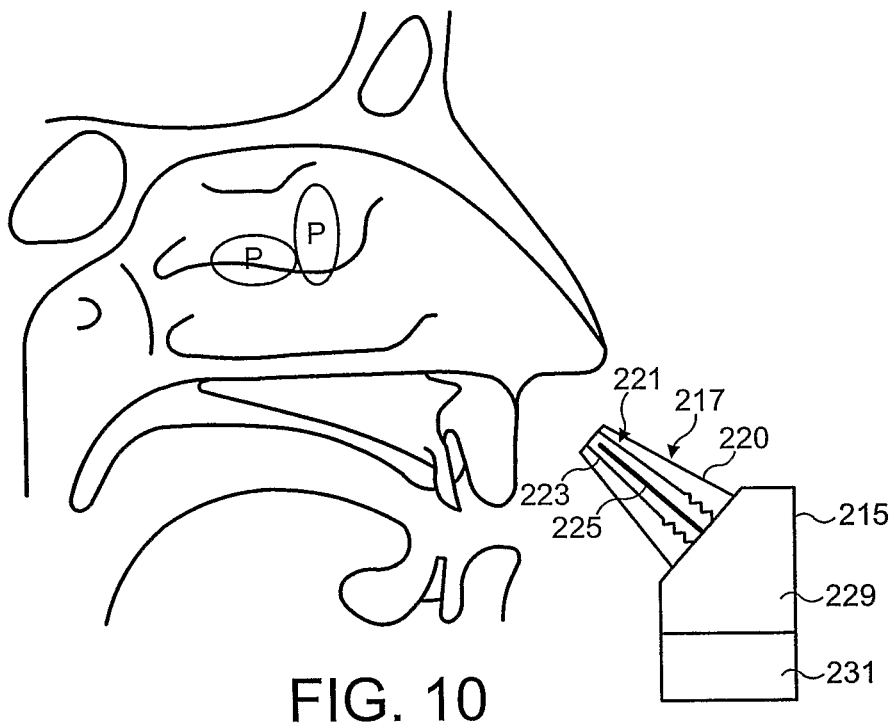
Figure 11:
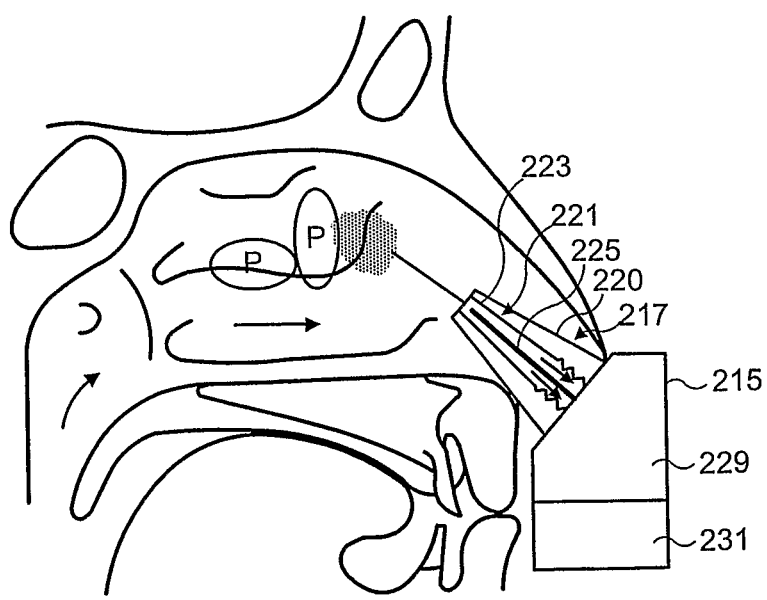

Preferred embodiments of the present invention will now be described hereinbelow by way of example only with reference to the accompanying drawings, in which:

FIG. 1 illustrates the segmentation of a nasal cavity in accordance with a preferred embodiment of the present invention;

FIG. 2 schematically illustrates a nasal delivery device in accordance with a first embodiment of the present invention;

FIG. 3 illustrates the delivery device of FIG. 2 where operative to deliver a dose of substance into the nasal airway of the subject;

FIG. 4 schematically illustrates a nasal delivery device in accordance with a second embodiment of the present invention;

FIG. 5 illustrates the delivery device of FIG. 4 where operative to deliver a dose of substance into the nasal airway of the subject;

FIG. 6 schematically illustrates a nasal delivery device in accordance with a third embodiment of the present invention;

FIG. 7 illustrates the delivery device of FIG. 6 where operative to deliver a dose of substance into the nasal airway of the subject;

FIG. 8 schematically illustrates a nasal delivery device in accordance with a fourth embodiment of the present invention;

FIG. 9 illustrates the delivery device of FIG. 8 where operative to deliver a dose of substance into the nasal airway of the subject;

FIG. 10 schematically illustrates a nasal delivery device in accordance with a fifth embodiment of the present invention; and FIG. 11 illustrates the delivery device of FIG. 10 where operative to deliver a dose of substance into the nasal airway of the subject.

FIGS. 2 and 3 illustrate a nasal delivery device in accordance with a first embodiment of the present invention.

The delivery device comprises a housing 15, a nosepiece unit 17 for fitting in a nasal cavity of a subject, and a mouthpiece 19 through which the subject exhales to actuate the delivery device.

The nosepiece unit 17 comprises a nosepiece 20, in this embodiment a frusto-conical element, for guiding the nosepiece unit 17 into a nasal cavity of the subject and being configured both to provide a fluid-tight seal with the nares of the nostril and at least obstruct, in this embodiment close, the nasal passage at a position therealong, in this embodiment at a position corresponding substantially to the nasal valve, thereby obstructing the anterior one-third of the nasal passage and leaving open the posterior two-thirds of the nasal cavity, as illustrated in FIG. 3.

In this embodiment the nosepiece 20 is further configured such as mechanically to open the nasal valve, thereby facilitating access to the posterior two-thirds of the nasal cavity, and in particular the middle meatus.

The nosepiece unit 17 further comprises an outlet unit 21 for delivering substance, which has an anti-inflammatory or other therapeutic effect on the middle meatus, into the nasal cavity of the subject and to the middle meatus, in this embodiment for the treatment of one or both of RS, in particular CRS, and polyposis. In this embodiment the substance comprises a formulation containing a nasal steroid, such as fluticasone.

In this embodiment the outlet unit 21 comprises a delivery channel 23 which is in fluid communication with the mouthpiece 19, such that an air flow is delivered into the nasal airway of the subject on exhalation by the subject through the mouthpiece 19, and a nozzle 25 for delivering substance into the nasal cavity of the subject.

In this embodiment the nozzle 25 is configured to deliver a jet, as a column of substance. In delivering the substance as a jet, the substance can be more readily directed at the middle meatus, typically as obstructed by RS and nasal polyps.

In this embodiment the nozzle 25 is configured to deliver a liquid jet, but in another embodiment could be configured to deliver a powder jet.

The delivery device further comprises a substance supply unit 29 for delivering metered doses of the substance, which is fluidly connected to the nozzle 25 to deliver the substance from the nosepiece unit 17, in this embodiment as a jet.

In this embodiment the substance supply unit 29 comprises a mechanical delivery pump.

In this embodiment the substance supply unit 29 is a multi-dose unit for delivering a plurality of metered doses of the substance. In another embodiment the substance supply unit 29 could be a single-dose unit for delivering a single metered dose of the substance.

The substance supply unit 29 is pre-primeable, in this embodiment by loading a resilient element, and includes a breath-actuated release mechanism 31 which, when triggered, releases the resilient element and actuates the substance supply unit 29 to deliver a metered dose of the substance through the nozzle 25.

In this embodiment the release mechanism 31 is configured to cause actuation of the substance supply unit 29 on generation of a predetermined pressure at the delivery channel 23.

The generation of a raised pressure in the nasal cavity acts to expand the region of the nasal cavity anterior of the middle meatus and posterior of the nasal valve, with one or both of inflamed mucosa or polyps in the upper region of the nasal cavity acting to provide a resistance to the anteriorly-delivered air flow and thus providing an increased pressure anterior of the middle meatus. This expansion of the region of the nasal cavity anterior of the middle meatus facilitates access to the middle meatus and also reduces the deposition of substance in the anterior region. Deposition in the anterior region has been shown to lead to crusting and bleeding, which is particularly uncomfortable. In addition, the increased pressure in the nasal cavity acts to force substance into ducts and channels leading to the sinuses, which can be blocked by mucosal inflammation and polyps.

Operation of the delivery device will now be described hereinbelow with reference to FIG. 3 of the accompanying drawings.

The nosepiece unit 17 is first inserted into one of the nasal cavities of a subject until the nosepiece 20 abuts the nares of the nostril such as to establish a fluid-tight seal therewith, at which point the distal end of the outlet unit 21 extends about 2 cm into the nasal cavity of the subject such as to engage with and expand the nasal valve, and the mouthpiece 19 is gripped in the lips of the subject.

The subject then begins to exhale through the mouthpiece 19, which exhalation acts to close the oropharyngeal velum of the subject and drive an air flow through the delivery channel 23 of the outlet unit 21, with the air flow passing into the one nasal cavity, around the posterior margin of the nasal septum and out of the other nasal cavity, thereby achieving a bi-directional air flow through the nasal airway of the subject, in the manner as described in WO-2000/051672. Where the middle meatus is obstructed, the flow is restricted and along the floor of the nose, but, as discussed hereinabove, acts to generate a pressure in the nasal cavity which acts to expand the constriction at the middle meatus.

In this embodiment, when the pressure developed at the delivery channel 23 reaches a predetermined value, the release mechanism 31 is triggered to actuate the substance supply unit 29 to deliver a metered dose of the substance to the nozzle 25 and into the nasal cavity of the subject as a jet.

In this embodiment the delivery device is configured such that at least 50% of the dose as initially deposited in the nasal cavity is deposited in a region of the nasal cavity which is posterior of the nasal valve, and at least 30% of the dose as initially deposited in the nasal cavity is deposited in an upper posterior region of the nasal cavity which is posterior of the nasal valve and above the inferior meatus. With such delivery, improved deposition is obtained on the middle meatus, in particular at the site of nasal polyps.

In preferred embodiments the delivery device is configured such that at least 55%, more preferably at least 60%, still more preferably at least 65% and yet more preferably 70% of the dose as initially deposited in the nasal cavity is deposited in the region posterior of the nasal valve.

In preferred embodiments the delivery device is configured such that at least 35%, more preferably at least 40%, still more preferably at least 45% and yet more preferably 50% of the dose as initially deposited in the nasal cavity is deposited in the upper posterior region of the nasal cavity.

In this embodiment, where the delivery device is a multi-dose device, the device is ready for further use following priming of the pump unit 29.

In one alternative embodiment the nozzle 25 could be configured to deliver a plurality of jets. This configuration still facilitates delivery through the nasal valve to the middle meatus as compared to conventional sprays which have a wide cone angle.

In one embodiment the contralateral nostril can be partially or wholly obstructed, such as to promote the generation of a raised pressure in the nasal cavity into which substance is to be delivered. In one embodiment the contralateral nostril can be obstructed by applying a pressure to the lateral nare of the contralateral nostril. In another embodiment the nosepiece unit 17 can include a second nosepiece 20 which is configured to be fitted in the other nostril of the subject such as to obstruct the same.

FIGS. 4 and 5 illustrate a nasal delivery device in accordance with a second embodiment of the present invention.

The delivery device of this embodiment is very similar to the delivery device of the above-described first embodiment, and thus, in order to avoid unnecessary duplication of description, only the differences will be described in detail, with like reference signs designating like parts.

The delivery device of this embodiment differs from that of the above-described first embodiment in further comprising an oral exhalation breath-actuatable gas supply unit 33 for delivering a gas flow through the delivery channel 23 of the outlet unit 21 in response to exhalation by a subject, and in that the mouthpiece 19 is in fluid communication with the gas supply unit 33 and not the delivery channel 23 of the outlet unit 21, whereby a gas flow is delivered to the delivery channel 23 of the outlet unit 21, and hence the nasal airway of the subject, in response to exhalation through the mouthpiece 19.

Operation of the delivery device is the same as for the above-described first embodiment, with a gas flow being delivered to the delivery channel 23 of the outlet unit 21 in response to exhalation through the mouthpiece 19.

In one alternative embodiment the release mechanism 31 could be a manually-actuated unit and the mouthpiece 19 omitted.

FIGS. 6 and 7 illustrate a nasal delivery device in accordance with a third embodiment of the present invention.

The delivery device of this embodiment is quite similar to the delivery device of the above-described first embodiment, and thus, in order to avoid unnecessary duplication of description, only the differences will be described in detail, with like reference signs designating like parts.

The delivery device of this embodiment differs from that of the above-described first embodiment in the release mechanism 31 being a manually-actuated unit and the mouthpiece 19 and the delivery channel 23 of the outlet unit 21 being omitted. With this configuration, a gas flow is not delivered into the nasal cavity of the subject, but the substance, in being delivered as a jet, acts to provide for targeted delivery to the middle meatus without any deposition anterior of the nasal valve, which would be experienced with a conventional nasal spray.

Operation of the delivery device is the same as for the above-described first embodiment, except that a gas flow is not delivered into the nasal cavity.

FIGS. 8 and 9 illustrate a nasal delivery device in accordance with a fourth embodiment of the present invention.

The delivery device comprises a housing 115, a nosepiece unit 117 for fitting in a nasal cavity of a subject, and a mouthpiece 119 through which the subject exhales to actuate the delivery device.

The nosepiece unit 117 comprises a nosepiece 120, in this embodiment a frusto-conical element, for guiding the nosepiece unit 117 into a nasal cavity of the subject and being configured both to provide a fluid-tight seal with the nares of the nostril and at least obstruct, in this embodiment close, the nasal passage at a position therealong, in this embodiment at a position corresponding substantially to the nasal valve, thereby obstructing the anterior one-third of the nasal cavity and leaving open the posterior two-thirds of the nasal cavity, as illustrated in FIG. 9.

In this embodiment the nosepiece 120 is further configured such as mechanically to open the nasal valve, thereby facilitating access to the posterior two-thirds of the nasal cavity, and in particular the middle meatus.

The nosepiece unit 117 further comprises an outlet unit 121 for delivering substance, which has an anti-inflammatory or other therapeutic effect on the middle meatus, into the nasal cavity of the subject and to the middle meatus, for the treatment of one or both of RS, in particular CRS, and polyposis. In this embodiment the substance comprises a formulation containing a nasal steroid, such as fluticasone.

In this embodiment the outlet unit 121 comprises a delivery channel 123 which is in fluid communication with the mouthpiece 119 such that an air flow is delivered into and through the nasal airway of the subject on exhalation by the subject through the mouthpiece 119, and a nozzle 125 for delivering the substance into the nasal cavity of the subject.

In this embodiment the nozzle 125 is configured to deliver an aerosol spray, either as a liquid or powder aerosol, here having a relatively-narrow cone angle.

In one embodiment the cone angle is not more than about 50 degrees, preferably not more than about 40 degrees, more preferably not more than about 35 degrees, still more preferably not more than about 30 degrees, yet more preferably not more than about 25 degrees, still yet more preferably not more than about 20 degrees, and still yet more preferably not more than about 15 degrees.

In delivering the substance as an aerosol spray with a narrow cone angle, the substance can be more readily directed at the middle meatus as obstructed by RS and nasal polyps.

The delivery device further comprises a substance supply unit 129 for delivering metered doses of the substance, which is fluidly connected to the nozzle 125 to deliver the substance from the nosepiece unit 117, in this embodiment as an aerosol spray.

In this embodiment the substance supply unit 129 comprises a mechanical delivery pump, in particular a liquid delivery pump or a powder delivery pump, which delivers metered doses of substance on actuation thereof.

In another embodiment the substance supply unit 129 could comprise a dry powder delivery unit which delivers metered doses of a substance, as a dry powder, on actuation thereof.

In a further embodiment the substance supply unit 129 could comprise an aerosol canister for delivering metered volumes of a propellant, preferably a hydrofluoroalkane (HFA) propellant or the like, containing substance on actuation thereof.

In another alternative embodiment the substance supply unit 129 could comprise a nebulizer which delivers metered doses of a substance, as an aerosol spray, on actuation thereof.

In this embodiment the substance supply unit 129 is a multi-dose unit for delivering a plurality of metered doses of the substance. In another embodiment the substance supply unit 129 could be a single-dose unit for delivering a single metered dose of the substance.

The substance supply unit 129 is pre-primeable, in this embodiment by loading a resilient element, and includes a breath-actuated release mechanism 131 which, when triggered, releases the resilient element and actuates the substance supply unit 129 to deliver a metered dose of the substance through the nozzle 125.

In this embodiment the release mechanism 131 is configured to cause actuation of the substance supply unit 129 on generation of a predetermined pressure at the delivery channel 123.

The generation of a raised pressure in the nasal cavity acts to expand the region of the nasal cavity anterior of the middle meatus and posterior of the nasal valve, with one or both of inflamed mucosa or polyps in the upper region of the nasal cavity acting to provide a resistance to the anteriorly-delivered air flow and thus providing an increased pressure anterior of the middle meatus. This expansion of the region of the nasal cavity anterior of the middle meatus facilitates access to the middle meatus and also reduces the deposition of substance in the anterior region. Deposition in the anterior region has been shown to lead to crusting and bleeding, which is particularly uncomfortable. In addition, the increased pressure in the nasal cavity acts to force substance into ducts and channels leading to the sinuses, which can be blocked by mucosal inflammation and polyps.

Operation of the delivery device will now be described hereinbelow with reference to FIG. 9 of the accompanying drawings.

The nosepiece unit 117 is first inserted into one of the nasal cavities of a subject until the nosepiece 120 abuts the nares of the nostril, such as to establish a fluid-tight seal therewith, at which point the distal end of the outlet unit 121 extends about 2 cm into the nasal cavity of the subject such as to engage with and expand the nasal valve, and the mouthpiece 119 is gripped in the lips of the subject.

The subject then begins to exhale through the mouthpiece 119, which exhalation acts to close the oropharyngeal velum of the subject and drive an air flow through the delivery channel 123 of the outlet unit 121, with the air flow passing into the one nasal cavity, around the posterior margin of the nasal septum and out of the other nasal cavity, thereby achieving a bi-directional air flow through the nasal airway of the subject, in the manner as described in WO-2000/051672. Where the middle meatus is obstructed, the flow is restricted and along the floor of the nose, but, as discussed hereinabove, acts to generate a pressure in the nasal cavity which acts to expand the constriction at the middle meatus.

In this embodiment, when the pressure developed at the delivery channel 123 reaches a predetermined value, the release mechanism 131 is triggered to actuate the substance supply unit 129 to deliver a metered dose of the substance to the nozzle 125 and into the nasal cavity of the subject as an aerosol spray.

In this embodiment the delivery device is configured such that at least 50% of the dose as initially deposited in the nasal cavity is deposited in a region of the nasal cavity which is posterior of the nasal valve, and at least 30% of the dose as initially deposited in the nasal cavity is deposited in an upper posterior region of the nasal cavity which is posterior of the nasal valve and above the inferior meatus. With such delivery, improved deposition is obtained on the middle meatus, in particular at the site In preferred embodiments the delivery device is configured such that at least 55%, more preferably at least 60%, still more preferably at least 65% and yet more preferably 70% of the dose as initially deposited in the nasal cavity is deposited in the region posterior of the nasal valve.

In preferred embodiments the delivery device is configured such that at least 35%, more preferably at least 40%, still more preferably at least 45% and yet more preferably 50% of the dose as initially deposited in the nasal cavity is deposited in the upper posterior region of the nasal cavity.

In this embodiment, where the delivery device is a multi-dose device, the device is ready for further use following priming of the pump unit 129.

In one embodiment the contralateral nostril can be partially or wholly obstructed, such as to promote the generation of a raised pressure in the nasal cavity into which substance is to be delivered. In one embodiment the contralateral nostril can be obstructed by applying a pressure to the lateral nare of the contralateral nostril. In another embodiment the nosepiece unit 117 can include a second nosepiece 120 which is configured to be fitted in the other nostril of the subject such as to obstruct the same.

FIGS. 10 and 11 illustrate a nasal delivery device in accordance with a fifth embodiment of the present invention.

The delivery device comprises a housing 215, and a nosepiece unit 217 for fitting in a nasal cavity of a subject and into which the subject nasally exhales to actuate the delivery device.

The nosepiece unit 217 comprises a nosepiece 220, in this embodiment a frusto-conical element, for guiding the nosepiece unit 217 into a nasal cavity of the subject and being configured both to provide a fluid-tight seal with the nares of the nostril and at least obstruct, in this embodiment close, the nasal passage at a position therealong, in this embodiment at a position corresponding substantially to the nasal valve, thereby obstructing the anterior one-third of the nasal cavity and leaving open the posterior two-thirds of the nasal cavity, as illustrated in FIG. 11.

In this embodiment the nosepiece 220 is further configured such as mechanically to open the nasal valve, thereby facilitating access to the posterior two-thirds of the nasal cavity, and in particular the middle meatus.

The nosepiece unit 217 further comprises an outlet unit 221 for delivering substance, which has an anti-inflammatory or other therapeutic effect on the middle meatus, into the nasal cavity of the subject and to the middle meatus, for the treatment of one or both of RS, in particular CRS, and polyposis. In this embodiment the substance comprises a formulation containing a nasal steroid, such as fluticasone.

In this embodiment the outlet unit 221 comprises a communication channel 223 which is in fluid communication with the nasal cavity of the subject, such as to enable nasal exhalation to be detected through the generation of an increased pressure thereat, and a nozzle 225 for delivering a metered dose of substance into the nasal cavity of the subject.

In this embodiment the nozzle 225 is configured to deliver a jet, as a column of substance, either of liquid or powder. In delivering the substance as a jet, the substance can be more readily directed at the middle meatus as obstructed by RS and nasal polyps.

The delivery device further comprises a substance supply unit 229 for delivering metered doses of the substance, which is fluidly connected to the nozzle 225 to deliver the substance from the nosepiece unit 217, in this embodiment as a jet.

In this embodiment the substance supply unit 229 comprises a mechanical delivery pump.

In this embodiment the substance supply unit 229 is a multi-dose unit for delivering a plurality of metered doses of the substance. In another embodiment the substance supply unit 229 could be a single-dose unit for delivering a single metered dose of the substance.

The substance supply unit 229 is pre-primeable, in this embodiment by loading a resilient element, and includes a breath-actuated release mechanism 231 which, when triggered by nasal exhalation, releases the resilient element and actuates the substance supply unit 229 to deliver a metered dose of the substance through the nozzle 225.

In this embodiment the release mechanism 231 is configured to cause actuation of the substance supply unit 229 on generation of a predetermined pressure at the communication channel 223, which is developed in response to nasal exhalation.

The generation of a raised pressure in the nasal cavity acts to expand the nasal cavity, and in particular the region including the middle meatus which represents a region of increased resistance when including one or both of inflamed mucosa or polyps. This expansion of the region of the nasal cavity including the middle meatus facilitates access to the middle meatus and also reduces the deposition of substance in the anterior region. Deposition in the anterior region has been shown to lead to crusting and bleeding, which is particularly uncomfortable. In addition, the increased pressure in the nasal cavity acts to force substance into ducts and channels leading to the sinuses, which can be blocked by mucosal inflammation and polyps.

Operation of the delivery device will now be described hereinbelow with reference to FIG. 11 of the accompanying drawings.

The nosepiece unit 217 is first inserted into one of the nasal cavities of a subject until the nosepiece 220 abuts the nares of the nostril, such as to establish a fluid-tight seal therewith, at which point the distal end of the outlet unit 221 extends about 2 cm into the nasal cavity of the subject such as to engage and expand the nasal valve.

The subject then begins to exhale nasally, which exhalation acts to generate an increased pressure in the one nasal cavity which acts to expand the constriction at the middle meatus. In this embodiment the mouth of the subject can be closed, or the mouth can remain open and the tongue be positioned such as to prevent oral exhalation, as illustrated in FIG. 11.

In this embodiment, when the pressure developed at the communication channel 223 reaches a predetermined value, the release mechanism 231 is triggered to actuate the substance supply unit 229 to deliver a metered dose of the substance to the nozzle 225 and into the nasal cavity of the subject as a jet.

In this embodiment the delivery device is configured such that at least 50% of the dose as initially deposited in the nasal cavity is deposited in a region of the nasal cavity which is posterior of the nasal valve, and at least 30% of the dose as initially deposited in the nasal cavity is deposited in an upper posterior region of the nasal cavity which is posterior of the nasal valve and above the inferior meatus. With such delivery, improved deposition is obtained on the middle meatus, in particular at the site of nasal polyps.

In preferred embodiments the delivery device is configured such that at least 55%, more preferably at least 60%, still more preferably at least 65% and yet more preferably 70% of the dose as initially deposited in the nasal cavity is deposited in the region posterior of the nasal valve.

In preferred embodiments the delivery device is configured such that at least 35%, more preferably at least 40%, still more preferably at least 45% and yet more preferably 50% of the dose as initially deposited in the nasal cavity is deposited in the upper posterior region of the nasal cavity.

In this embodiment, where the delivery device is a multi-dose device, the device is ready for further use following priming of the pump unit 229.

In one alternative embodiment the nozzle 225 could be configured to deliver a plurality of liquid jets. This configuration still facilitates delivery through the nasal valve to the middle meatus as compared to conventional sprays which have a wide cone angle.

In one embodiment the contralateral nostril can be partially or wholly obstructed, such as to promote the generation of a raised pressure in the nasal cavity into which substance is to be delivered. In one embodiment the contralateral nostril can be obstructed by applying a pressure to the lateral nare of the contralateral nostril. In another embodiment the nosepiece unit 217 can include a second nosepiece 220 which is configured to be fitted in the other nostril of the subject such as to obstruct the same.

Finally, it will be understood that the present invention has been described in its preferred embodiment and can be modified in many different ways without departing from the scope of the invention as defined by the appended claims.

In one modification, the delivery device of the fifth-described embodiment could be modified to include first and second nosepiece units 217 for fitting to the respective nostrils of the subject. With this configuration, an increased pressure is generated in both of the nasal cavities and substance can be delivered to both of the nasal cavities in a single operation of the delivery device.

In another modification, the delivery device of the fifth-described embodiment could be modified, in the manner of the fourth-described embodiment, such that the outlet unit 221 provides for an aerosol spray, either as a liquid or powder aerosol.

In preferred embodiments the delivery devices are configured to deliver an air flow through one nostril of a subject at such a pressure as to flow around the posterior margin of the nasal septum and out of the other nostril of the subject, thereby achieving bi-directional delivery through the nasal cavities as disclosed in WO-A-00/51672, the content of which is herein incorporated by reference. In alternative embodiments the delivery device could be configured to deliver an air flow at a reduced pressure which is not sufficient to achieve bidirectional delivery through the nasal cavities. Such embodiments are still advantageous as compared to known delivery devices in providing for velum closure and being capable of achieving targeted delivery.

REFERENCES

1. Cole, P, The Respiratory Role of the Upper Airways, a selective clinical and pathophysiological review. 1993, Mosby-Year Book Inc. ISBN 1.55664-390-X.
2. Rosenberger, H, Growth and Development of the Naso-Respiratory Area in Childhood, PhD Thesis, Laboratory of Anatomy, School of Medicine, Western Reserve University, Presented to the Annual Meeting of the American Laryngological, Rhinological and Otological Society, Charleston, South Carolina, USA, 1934.
3. Zacharek, M A et al, Sagittal and Coronal Dimensions of the Ethmoid Roof: A Radioanatomic Study, Am J Rhinol 2005, Vol 19, pages 348 to 352.

The invention claimed is:

1. A method of delivering fluticasone to a middle meatus in a nasal airway of a subject in treatment of rhinosinusitis or nasal polyps in the subject in the need thereof, the method comprising:
    inserting a nosepiece unit into a first nostril of the subject, the nosepiece unit including a nosepiece and a nozzle through which the fluticasone is delivered to a nasal cavity of the subject from a substance supply unit, which comprises a manually-actuated liquid delivery pump;
    the subject exhaling through a mouthpiece, which is fluidly connected to the nosepiece, so as to cause closure of an oropharyngeal velum of the subject and deliver an exhalation air flow through the first nostril, around a posterior margin of a nasal septum and out of a second nostril of the subject; and
    manually actuating the liquid delivery pump to deliver, during exhalation through the mouthpiece, a liquid aerosol spray comprising a dose of fluticasone from the substance supply unit through the nozzle into the cavity;
    wherein the nosepiece is inserted into the first nostril such that the nosepiece extends into a nasal valve and expands the nasal valve, and the nozzle delivers the dose of fluticasone as at least one liquid jet or liquid aerosol spray having a cone angle of not more than about 50 degrees, whereby at least 50% of the dose of fluticasone as initially deposited in the cavity is deposited in a region of the cavity which is posterior of the nasal valve of the subject and at least 30% of the dose of fluticasone as initially deposited in the cavity is deposited in an upper posterior region of the cavity which is posterior of the nasal valve and above an inferior meatus of the subject.

2. The method of claim 1, wherein the nosepiece is configured to obstruct the nasal valve when the nosepiece is inserted into the first nostril, and thereby prevent deposition of substance anteriorly of the nasal valve.

3. The method of claim 1, wherein at least 55% of the dose as initially deposited in the cavity is deposited in a region posterior of the nasal valve.

4. The method of claim 3, wherein at least 60% of the dose as initially deposited in the cavity is deposited in the region posterior of the nasal valve.

5. The method of claim 4, wherein at least 65% of the dose as initially deposited in the cavity is deposited in the region posterior of the nasal valve.

6. The method of claim 5, wherein at least 70% of the dose as initially deposited in the cavity is deposited in the region posterior of the nasal valve.

7. The method of claim 1, wherein at least 35% of the dose as initially deposited in the cavity is deposited in the upper posterior region thereof.

8. The method of claim 7, wherein at least 40% of the dose as initially deposited in the cavity is deposited in the upper posterior region thereof.

9. The method of claim 8, wherein at least 45% of the dose as initially deposited in the cavity is deposited in the upper posterior region thereof.

10. The method of claim 9, wherein at least 50% of the dose as initially deposited in the cavity is deposited in the upper posterior region thereof.

11. The method of claim 1, wherein the method comprises treating acute rhinosinusitis in the subject in need thereof.

12. The method of claim 1, wherein the method comprises treating chronic rhinosinusitis in the subject in need thereof.

13. The method of claim 1, wherein the nozzle delivers a liquid aerosol spray having a cone angle of not more than about 40 degrees.

\* \* \* \* \*

UNITED STATES PATENT AND TRADEMARK OFFICE
CERTIFICATE OF CORRECTION

| | |
|---|---|
| PATENT NO. | : 12,083,270 B2 |
| APPLICATION NO. | : 12/279285 |
| DATED | : September 10, 2024 |
| INVENTOR(S) | : Per Gisle Djupesland et al. |

It is certified that error appears in the above-identified patent and that said Letters Patent is hereby corrected as shown below:

In the Claims

Claim 1, Column 14, Lines 21-22, "the cavity" should read --the nasal cavity--.

Claim 1, Column 14, Line 29, "the cavity" should read --the nasal cavity--.

Claim 1, Column 14, Line 30, "the cavity" should read --the nasal cavity--.

Claim 1, Column 14, Line 32, "the cavity" should read --the nasal cavity--.

Claim 1, Column 14, Line 33, "the cavity" should read --the nasal cavity--.

Claim 3, Column 14, Line 41, "the cavity" should read --the nasal cavity--.

Claim 4, Column 14, Line 44, "the cavity" should read --the nasal cavity--.

Claim 5, Column 14, Line 47, "the cavity" should read --the nasal cavity--.

Claim 6, Column 14, Line 50, "the cavity" should read --the nasal cavity--.

Claim 7, Column 14, Line 53, "the cavity" should read --the nasal cavity--.

Claim 8, Column 14, Line 56, "the cavity" should read --the nasal cavity--.

Claim 9, Column 14, Line 59, "the cavity" should read --the nasal cavity--.

Claim 10, Column 14, Line 62, "the cavity" should read --the nasal cavity--.

Signed and Sealed this
Fifteenth Day of October, 2024

Katherine Kelly Vidal
*Director of the United States Patent and Trademark Office*